United States Patent [19]

McClure et al.

[11] Patent Number: 5,212,084
[45] Date of Patent: May 18, 1993

[54] RETROVIRUS AND RELATED METHOD USED FOR PRODUCING A MODEL FOR EVALUATING THE ANTIRETROVIRAL EFFECTS OF DRUGS AND VACCINES

[75] Inventors: Harold M. McClure; Patricia N. Fultz, both of Atlanta; Daniel C. Anderson, Stone Mountain, all of Ga.

[73] Assignees: Emory University; Centers for Disease Control, both of Atlanta, Ga.

[21] Appl. No.: 200,843

[22] Filed: Jun. 1, 1988

[51] Int. Cl.$^5$ ............................ C12N 7/00; C12N 7/08
[52] U.S. Cl. .................................. 435/235.1; 435/237
[58] Field of Search ...................... 435/235, 237, 235.1; 800/2, DIG. 5

[56] References Cited

PUBLICATIONS

Lowenstine et al., Int. J. Cancer 38(4): 563–574 (1986).
Franchini, G. et al.; Nature, 328:539–543 (Aug. 1987).
Hu, Shiu-Lok et al.; Nature, 328:721–723 (Aug. 1987).
Fultz, P. N. et al.; Vaccines 88:167–170 (May 1988).
Fultz, P. N., et al.; Proc. natl. Acad. Sci. USA, 83:5286–5290 (Jul. 1986).
Letvin, N. L. et al.; Science, 230:71–73 (Oct. 1985).
Alizon, M. et al.; Nature, 312: 757–760 (Dec. 1984).
Clavel, F. et al.; Nature, 324:691–695 (Dec. 1986).
Guyader, M. et al.; Nature 326:662–669 (Apr. 1987).
Fultz, P. et al.; Abstracts of symposium on nonhuman primate models for the acquired immunodeficiency syndrome, Atlanta, Ga.; p. 14 (Oct. 1987).
Anderson, D. et al.; Abstracts of Symposium on Nonhuman Primate Models for the Acquired Immunodeficiency Syndrome, Atlanta, Ga.; p. 8 (Oct. 1987).
McClure, H. et al.; Abstracts of Symposium on Nonhuman Primate Models for the Acquired Immunodeficiency Syndrome Atlanta, Ga.; p. 11 (Oct. 1987).
Fultz, P. N. et al.; Abstracts of the VII International Congress of Virology, Alberta, Canada; p. 165 (Aug. 1987).
McClure, H. M. et al.; Proceedings of the III International Conference on AIDS, Washington, D.C.; p. 212 (Jun. 1987).
Fultz, P. N. and Morrow, W.; In *AIDS and other Manifestations of HIV Infection* (ed. G. P. Wormser) Noyes Pub., New Jersey; pp. 257–269 (1987).
Chakrabarti, L. et al.; Nature, 328:543–547 (Aug. 1987).

Primary Examiner—Elizabeth C. Weimar
Assistant Examiner—Jasemine C. Chambers
Attorney, Agent, or Firm—Needle & Rosenberg

[57] ABSTRACT

A retrovirus and related method used in producing a model for evaluating the antiretroviral effects of drugs and vaccines includes the steps of removing T-lymphotropic retrovirus from a first simian primate which has developed disease over a first period of time, the disease being attributable to the retrovirus, and placing the retrovirus into a second simian primate to induce acute disease in the second simian primate over a second period of time which is shorter than the first period.

1 Claim, 3 Drawing Sheets

RETROVIRUS AND RELATED METHOD USED FOR PRODUCING A MODEL FOR EVALUATING THE ANTIRETROVIRAL EFFECTS OF DRUGS AND VACCINES

The Government has rights in this invention pursuant to NIH Grant RR00165.

BACKGROUND OF THE INVENTION

The present invention relates to the health research industry, and more particularly to a method for providing a model in which the efficacy of antiretroviral drugs and vaccines can be determined in a relatively short time, as well as a retrovirus used therein.

An important step in the development of any vaccine is testing that vaccine for efficacy in the prevention of infection and/or disease. Testing for efficacy, as well as for safety and immunogenicity, is facilitated by the use of animal models, especially in cases where the potential success of a vaccine is questionable. Because of the world-wide spread of the human immunodeficiency virus (HIV) and the fact that HIV is associated with a disease with essentially 100% mortality, the need for a vaccine against HIV is self-evident. Almost from the time that HIV was identified as the etiologic agent of acquired immunodeficiency syndrome (AIDS), it has been apparent that the generation of a vaccine might be difficult for at least two reasons. First, no fully efficacious vaccine against a retrovirus, and none against a lentivirus, exists and second, all HIV isolates differ from one another in nucleotide sequence, which suggested they might also differ significantly at the antigenic level. These factors emphasize the potential importance of animal models that could be used to test putative vaccines for efficacy, especially those that reproduced the natural history of and disease progression resulting from HIV infection.

The major requirements for an animal model to be useful in vaccine efficacy studies are that (i) essentially all animals become infected following innoculation of virus; (ii) infection be easily detected by isolation of virus, which can be quantitated; (iii) seroconversion occurs; and (iv) infection elicits disease, preferably analogous to disease induced by the same virus in humans. The latter is important if the vaccine does not provide absolute protection against infection, in which case one could monitor and assess the effects of the putative vaccine on prevention or the severity of the ensuing disease.

A major obstacle to researchers has been the lack of a model which provides a means to quickly determine the efficacy of newly developed antiretroviral drugs and vaccines, and particularly those associated with AIDS. This is primarily because there exists no previously identified immunodeficiency virus capable of causing acute disease and death within a few days after infection.

Therefore, a need exists for a model in which the efficacy of antiretroviral drugs and particularly those associated with human immunodeficiency virus, can be determined in a very short time.

There also exists a need for such a model which provides a means for quickly evaluating antiretroviral vaccines There exists a further need for a retrovirus capable of being utilized in producing such a model.

SUMMARY OF THE INVENTION

The present invention relates to a model for rapidly evaluating the antiretroviral effects of drugs and vaccines.

A highly virulent strain of a simian immunodeficiency virus (a T-lymphotropic retrovirus), herein termed "SIV/SMM/PBg14", was obtained from the tissues of a first pig-tailed macaque that had been inoculated with the virus approximately 14 months earlier. The macaque developed chronic diarrhea, lymphadenopathy, splenomegaly, lymphopenia and thrombocytopenia, and also became terminally anemic and ataxic. Blood was taken from the first infected macaque and transfused to second macaques. The majority of these second macaques died in about 7 to 9 days after transfusion. Prior to death, i.e., about 5 days after transfusion, the second macaques developed acute disease with symptoms that included lymphadenopathy, splenomegaly and hyperplasia, and hemorrhage and necrosis of lymphoid tissue. Histologically, the lymphoid tissues became reactive and contained foci of necrosis and multinucleated giant cells. Moreover, virus could be isolated from multiple tissues, including the brain. Similar results were obtained by repeating the inoculation step with a retrovirus isolated from tissues of either the initial macaque or the transfusion recipients.

It is an object of the present invention, therefore, to provide a model in which the efficacy of antiretroviral drugs and particularly those related to the human immunodeficiency virus, can be determined in a very short time.

It is also an object of the present invention to provide a means for quickly evaluating antiretroviral vaccines. It is a further object of this invention to provide a retrovirus capable of being used to provide such a model.

These and other objects and advantages are described in the following detailed description of a preferred embodiment of the present invention.

DETAILED DESCRIPTION OF A PREFERRED EMBODIMENT

Figure 1:
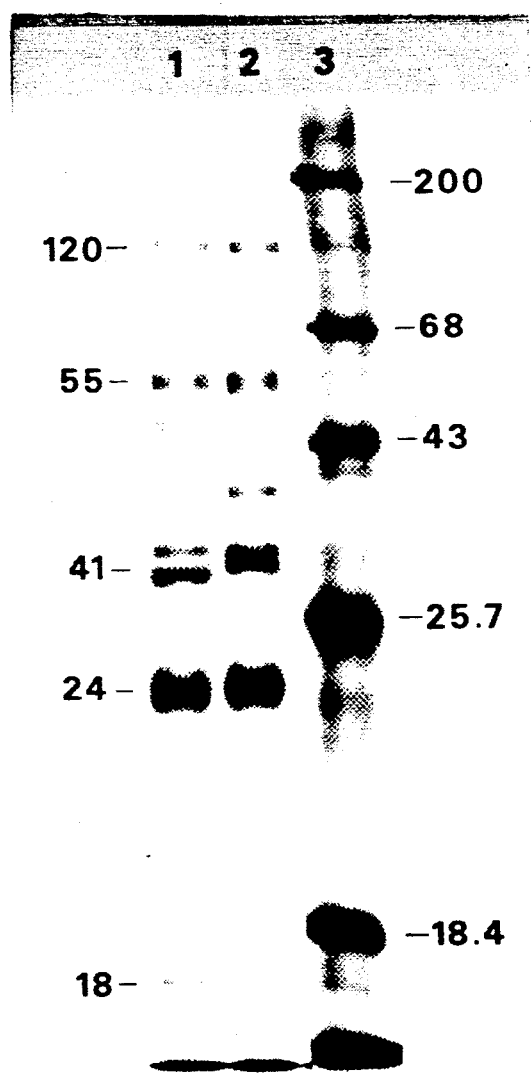
FIG. 1 is a gel showing a comparison of SIV/SMM and HIV gene products by RIP assay. Proteins from PHA-AWBC infected with SIV/SMM (lane 1) or HIV (lane 2) were immunoprecipitated with rabbit antiserum to HIV (CDC isolate 451). Lane 3: $^{14}$C-labeled molecular weight markers.

I. Isolation of a T-lymphotropic retrovirus from naturally infected cercocebus ATYS A virus, herein termed "SIV/SMM" for simian immunodeficiency virus/sooty mangabey monkey, has been isolated from healthy sooty mangabey monkeys (*Cercocebus atys*), which are indigenous to Central and Western Africa.

A. MATERIALS AND METHODS

1. Animals. The Yerkes Regional Primate Research Center in Atlanta, Ga. maintains a colony of approximately 120 colony-born or wild-caught mangabey monkeys. The 15 animals used in this study were selected at random from among mangabey monkeys that are housed together in an indoor/outdoor facility. The mangabeys selected from the colony were between 4 and 22 years old, and all were colony-born except for nos. 2 and 8 (see Table I). Blood was collected to obtain peripheral blood mononuclear cells (PBMC) and serum. None of the animals was neutropenic or lymphopenic, and all were clinically normal at the time of blood collection.

2. Isolation of Virus. Virus was isolated from PBMC of mangabeys by coculturing PBMC with phytohemagglutinin P-stimulated adult human leukocytes (PHA-AWBC). All of the viruses identified herein are deposited at the Yerkes Regional Primate Research Center, Atlanta, Georgia. Cell-free supernatants from cocultures were monitored for $Mg^{2+}$-dependent reverse transcriptase activity. Culture supernatants with positive reverse transcriptase were tested for their ability to transfer infectivity to fresh PHA-AWBC or to established cell lines; some of the initial cocultures were tested by electron microscopy for the presence of virus.

3. Cellular Tropism. The cellular tropism of SIV/SMM was determined in two ways. First, PHA-AWBC were infected with an isolate of SIV/SMM and, periodically, the number of T-helper (T4) and T-cytotoxic/suppressor cells (T8) in the infected culture and in an uninfected control culture were determined by indirect immunofluorescence assay (IFA) using a T-helper/suppressor ratio test kit (Becton Dickinson). At least 500 cells were counted for each determination. Reverse transcriptase activity in both cultures was also assayed and, in the infected culture, peaked at $>10^6$ cpm per reaction, while that in the control culture never exceeded 1400 cpm. Second, the ability of isolates of SIV/SMM to replicate in established cell lines of different lineages was tested. Approximately $10^5$ cpm of SIV/SMM reverse transcriptase activity was used to infect $10^7$ cells. Culture supernatants were monitored for reverse transcriptase activity. The cell line HT was provided by R. C. Gallo (National Institutes of Health); HUT78 and 6D5, a subclone of HUT78, by J. Getchell (Centers for Disease Control); and K562, by S. McDougal (Centers for Disease Control).

4. Serologic Assays. Mangabey serum samples were tested at a 1:50 dilution by enzyme immunoassay (EIA) using Abbott Laboratories HTLV-III EIA kit, at a 1:100 dilution by immunoblot using H9/HTLV-III antigen, and at a 1:20 dilution for SIV/SMM-specific antibodies by indirect IFA using acetone-fixed, virus-infected PHA-AWBC. The second antibody was a fluorescein-labeled goat anti-monkey IgG (Cooper Biomedical, Malvern, Pa).

5. Neutralization Assay. Serum samples from the 15 mangabeys were screened at a 1:10 dilution for neutralizing activity against SIV/SMM; some of the sera were tested against the LAV strain of HIV. In addition, serum with LAV-neutralizing activity that had been obtained from a chimpanzee infected with LAV was tested for its ability to neutralize SIV/SMM. Approximately $4 \times 10^3$ cpm of viral reverse transcriptase activity (LAV or SIV/SMM) was incubated with serum in RPMI 1640 medium for 60 minutes at room temperature (total volume, 0.5 ml). The virus/antibody mixture was then used to infect $10^7$ PHA-AWBC in 2.5 ml of medium B (RPMI containing 10% fetal bovine serum, interleukin 2, and DEAE-dextran). After overnight adsorption, the cells were washed and resuspended in 15 ml of medium B. Culture supernatants were monitored for extracellular reverse transcriptase activity on days 6, 9, 12, and 16. Neutralizing antibody activity was considered to be present if there was at least 80% inhibition of reverse transcriptase activity compared to reverse transcriptase activity in control cultures.

6. Nucleic Acid Hybridization. Concentrated virus, prepared from SIV/SMM-infected cell culture supernatants, was lysed, spotted onto nitrocellulose filters, and hybridized to genomic (approximately 9-kilobase) HIV (clone Zr6; Srinivasan et al., *Gene* Vol. 52, pp. 71-82 (1987) as described in Alizon, M., Sonigo, P., Barre-Sinoussi, F., Cjhermann, J. C., Tiollais, P., Montagnier, L. & Wain-Hobson, S. (1984) *Nature* (London) 312, 756-760. High molecular weight DNA was isolated from SIV/SMM-infected cells and digested with several restriction enzymes before it was used with the Zr6 cDNA clone of HIV in Southern hybridization assays.

B. RESULTS

1. Incidence of Disease in the Mangabey Colony. Since the mangabey colony was established at the Yerkes Primate Center, there has been no apparent difference in the incidence of disease in this species when compared with the incidence of disease in other species of monkeys at the Yerkes field station. During the past 16 years, 55% (42 animals) of the deaths in the mangabey colony resulted from spontaneous disease problems in animals older than 1 month. Neoplastic diseases were not found in any of these animals, and lymphadenopathy of one or more lymph node groups was seen in only six animals. Thus, it appears that SIV/SMM infection of mangabeys does not cause a significant degree of immunodeficiency with opportunistic infections and lymphomas as occurs in rhesus macaques infected with STLV-III.

2. *Isolation of Virus.* Virus was detected in cocultures of PHA-AWBC and PBMC from 14 of 15 randomly selected mangabeys, as seen in Table 1 Reverse transcriptase activity was detected in initial cultures as early as 6 days and as late as 23 days after establishing the cocultures, and peak reverse transcriptase activity reached $>3 \times 10^6$ cpm/ml Cell-free supernatants of positive cultures transferred infectivity to fresh PHA-AWBC Examination of cultures by thin-section electron microscopy showed retrovirus particles with eccentric nucleoids that were morphologically indistinguishable from HIV, STLV-III, and STLV-III$_{AGM}$.

3. Retrospective Analysis of Serum from Mangabeys at the Yerkes Primate Center. Serum obtained in 1981 and 1983 from mangabeys at Yerkes was analyzed to determine how long SIV/SMM had been present in the colony. As shown by indirect IFA, SIV/SMM-specific antibodies were present in serum samples obtained from 9 of 11 (82%) and 7 of 11 (64%) mangabeys in 1981 and 1983, respectively. Therefore, SIV/SMM infection was probably widespread in the mangabey colony before 1981. Four of the stored serum samples tested retrospectively were from animals in this study. Serum that was obtained from mangabey 1 (Table 1) in 1983 did not have detectable antibodies to SIV/SMM, indicating that seroconversion in this animal occurred between 1983 and Jun. 1985, when the current study began. However, sera obtained in 1981 from mangabeys 3, 5 and 14 (Table 1) were positive for antibodies to SIV/SMM. All four of these animals were colony-born between 1970 and 1976, and none of these animals has had any significant clinical problems.

4. Antibody Cross-Reactivity to SIV/SMM and HIV. At a serum dilution of 1:50, 2 of the 15 mangabey serum samples were positive by EIA for antibodies to HIV. In contrast, 11 of the 15 mangabey serum samples had antibodies that bound HIV p24 by immunoblot assay (using a minigel system that identifies antibodies to the viral proteins p18, p24 and gp41) (Table 1). That the human and mangabey retroviruses had antigenic determinants that were related was supported by data from RIP assays that were done with various types of serum and PHA-AWBC infected with SIV/SMM or HIV.

When serum from the 15 mangabeys was tested by indirect IFA, all 14 virus-positive animals had antibodies that bound to SIV/SMM-infected cells but not to uninfected cells. Serum from the single virus-negative animal was negative for antibodies to SIV/SMM and showed no reactivity to HIV by EIA and immunoblot Table 1. Serum samples from three LAV-infected chimpanzees reacted with LAV- and SIV/SMM-infected cells by IFA, while serum samples from uninfected chimpanzees were negative in the same assays. When SIV/SMM-specific antisera were tested against LAV-infected cells, little or no reactivity was observed.

Figure 2:
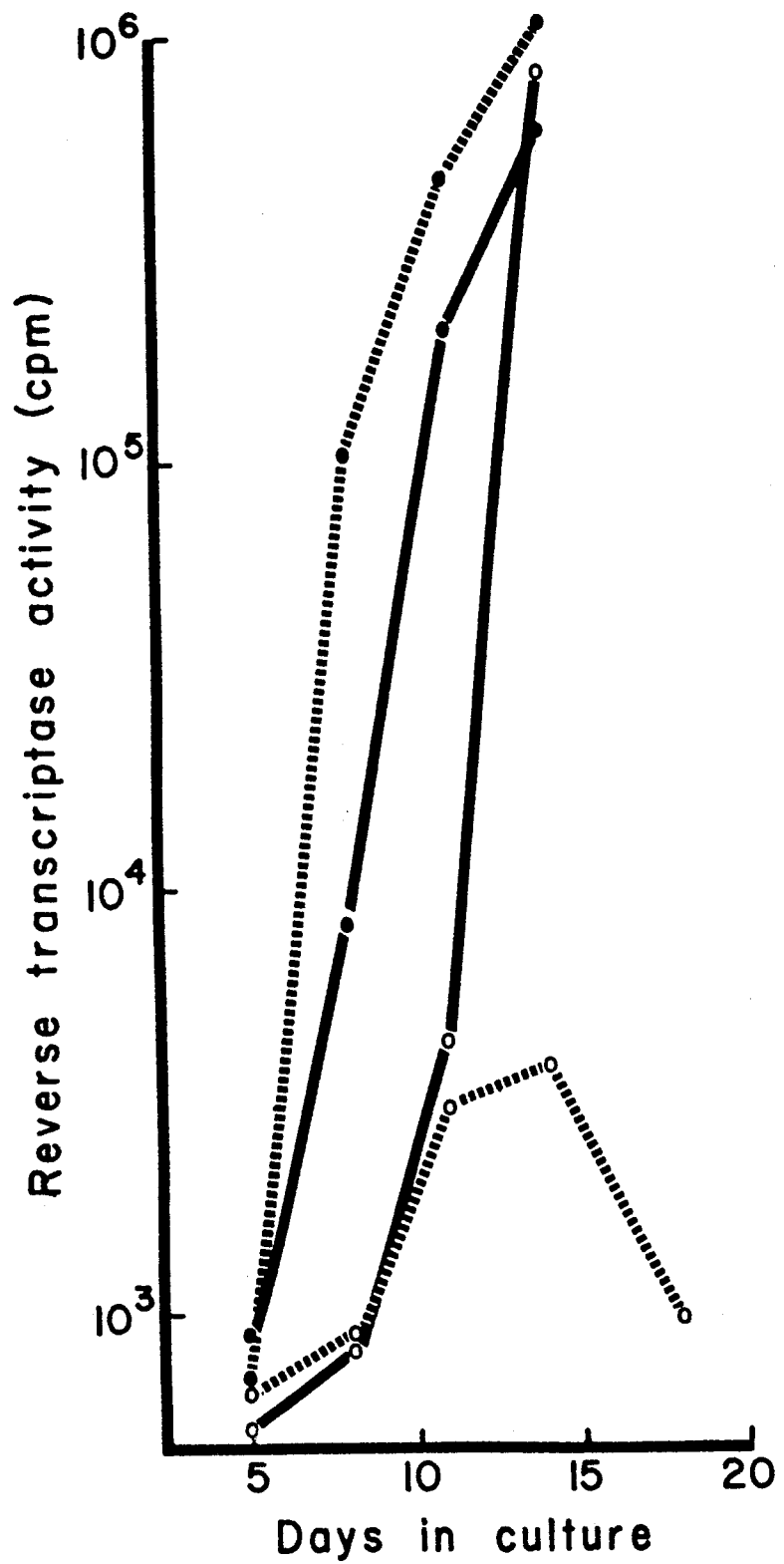
FIG. 2 is a graph illustrating the results of neutralization of SIV/SMM of the present invention and LAV by antiserum elicited by LAV; SIV/SMM (—) and LAV (— — —) were incubated with serum from a LAV-infected chimpanzee (o) or with serum from mangabey 14 (•) prior to infection of PHA-AWBC.

5. Neutralization of SIV/SMM. Serum samples from all 15 mangabeys were tested for neutralizing activity against the SIV/SMM isolate from mangabey 3 (FIG. 1). Very little, if any, neutralizing activity was detected in any of the sera at the dilution used (1:10). At this dilution, none of the serum samples from the persistently infected mangabeys completely neutralized SIV/SMM. Because HIV-specific antiserum immunoprecipitated some of the SIV/SMM proteins, an investigation was made as to whether serum that neutralized HIV also neutralized SIV/SMM. A chimpanzee (C-560) serum sample that had a neutralizing titer of approximately 300 against LAV (P.N.F., unpublished work) was used. In a representative experiment, a 1:10 dilution of the anti-LAV serum from chimpanzee C-560 completely neutralized LAV and showed some neutralizing activity against SIV/SMM (FIG. 2). After 11 days in culture, reverse transcriptase activity in the culture (determined as cpm) established after incubation of SIV/SMM with LAV-specific antiserum was decreased by 98% compared to that in the culture established after incubation of SIV/SMM with mangabey serum. Serum from mangabey 14 had a slight effect on the replication of SIV/SMM but no effect on the replication of LAV. Serum obtained from C-560 prior to LAV infection did not neutralize either LAV or SIV/SMM and resulted in virus growth curves similar to those obtained with serum from mangabey 14 (FIG. 2).

6. Nucleic Acid Homology Between SIV/SMM and HIV. Homology at the nucleic acid level between two mangabey virus isolates and HIV was not detected using two different techniques at high- and low-stringency conditions. Dot-blot hybridization of SIV/SMM viral RNA with a 9-kilobase clone of HIV showed no detectable RNA-DNA sequency homology between SIV/SMM and HIV. In addition, Southern hybridization of cloned HIV and high molecular weight DNA, isolated from SIV/SMM-infected cells and digested with a battery of restriction enzymes, confirmed that there was no detectable homology between SIV/SMM and HIV at the DNA·DNA level.

Figure 3:
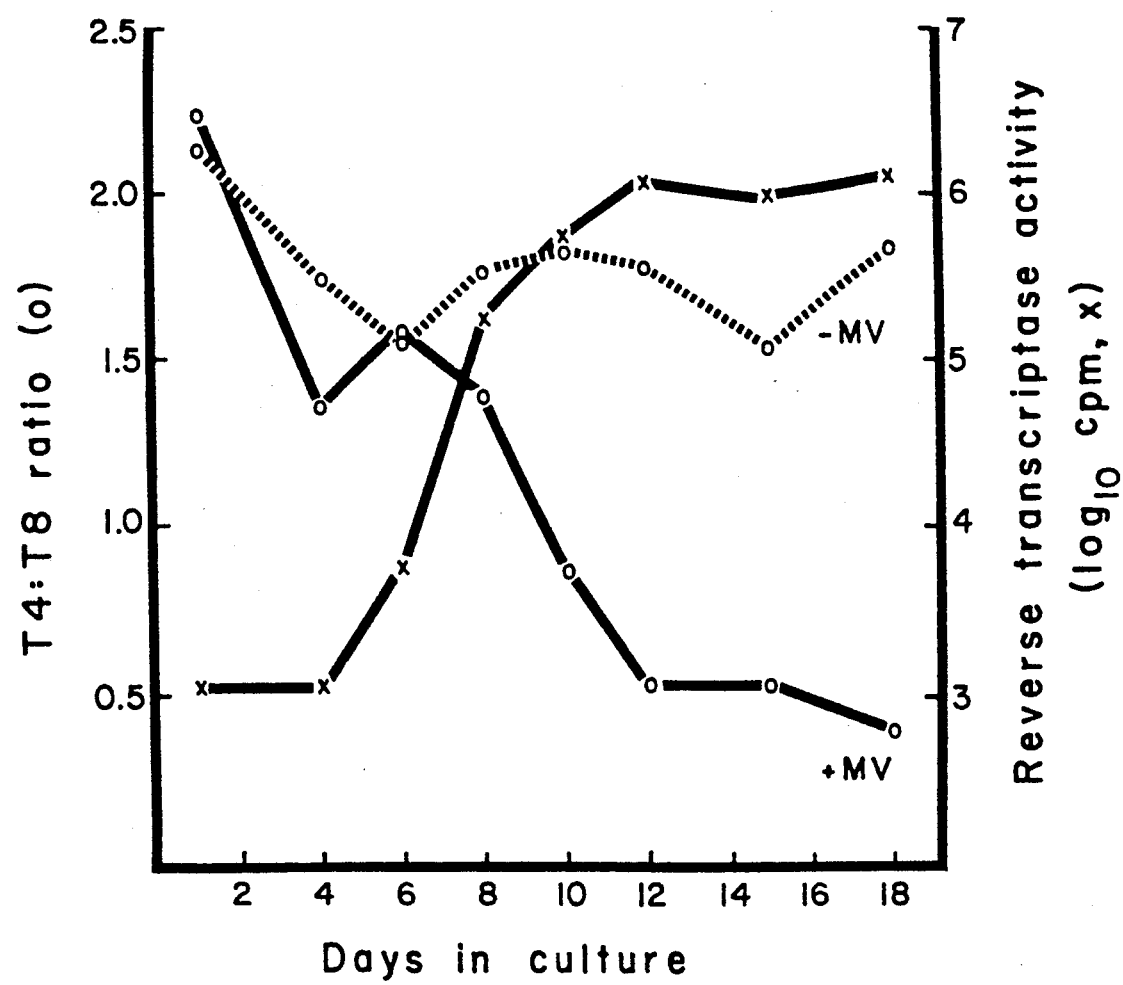
FIG. 3 is a graph illustrating the cytopathic effect of SIV/SMM of the present invention on helper T-lymphocytes; samples of PHA-AWBC that were either uninfected (O— — —O) or infected O-O) with SIV/SMM from mangabey 7 were taken at 2- to 3-day intervals and assayed for numbers of helper (T4) and suppressor (T8) T cells and for reverse transcriptase activity (x) present in the culture.

7. Cellular Tropism of SIV/SMM. PHA-AWBC were infected with SIV/SMM; periodically, the number of helper (T4) and cytotoxic/suppressor (T8) cells and particulate reverse transcriptase activity were determined. Although the T4/T8 ratio in a control culture remained essentially constant, the number of T4 cells and, thus, the T4/T8 ratio in infected cultures decreased as the reverse transcriptase activity increased (FIG. 3). During the 18 days of assay, the total number of T4 and T8 cells decreased in both cultures, but the greatest decrease was in the number of T4 cells in the SIV/SMM-infected culture. Although infection of T4 cells was not demonstrated directly, the data indicate that SIV/SMM infection of human PBMC results in a loss of T4 cells. In addition, some isolates of SIV/SMM replicated to high titers in the T-cell lines HUT78, HT, and 6D5, but no isolates infected the K562 myeloid cell line or the Raji B-cell line. Although all SIV/SMM isolates replicated in PHA-AWBC, some isolates did not grow in all T-cell lines. In order to reach maximum reverse transcriptase values, SIV/SMM cultures were maintained for a longer time than was required for a similar inoculum of HIV.

8. Replication of SIV/SMM in PBMC from *Rhesus Macaques.* SIV/SMM replicated to high titer in vitro in PBMC from rhesus macaques, but there has not been detection of the replication of LAV or ARV-2 in vitro or in vivo in cells from rhesus macaques Table 2.

C. DISCUSSION

Approximately 80% of healthy mangabey monkeys from a colony with no unusual incidence of disease were found to be infected with a T-lymphotropic retrovirus, designated SIV/SMM, that is similar to the human virus HIV and the simian viruses STLV-III and STLV-IIIAGM. All of the animals from which virus was isolated had serum antibodies that reacted with SIV/SMM-infected cells in IFAs, but the antibodies had little, if any, neutralizing activity. Persons infected with HIV also have been reported to have low serum neutralizing-antibody titers. Antibodies from some mangabeys were cross-reactive with HIV p24 by immunoblot and immunoprecipitated HIV p24, which is encoded in the gag region of the viral genome, in RIP assays. It is also of interest that the cross-reactivity of antibodies to HIV for SIV/SMM included neutralizing antibodies.

II. INFECTION OF PRIMATES WITH SIMIAN IMMUNODEFICIENCY VIRUSES

A. PROCEDURE

To determine the pathogenicity of the mangabey virus (SIV/SMM) for other nonhuman primate species, and to establish a more readily available nonhuman primate species as a model for the study of HIV infection, 12 rhesus and one pig-tailed macaque were inoculated intravenously with approximately $10^4$ TCID of SIV/SMM. The animals ranged from 1 to 15 months of age at the time of inoculation. Twelve of 13 inoculated animals became virus positive and seroconverted within 3 to 6 weeks of inoculation and have remained virus positive for periods of 18 to 31 months post-inoculation. Infected animals have shown variable degrees of peripheral lymphadenopathy, splenomegaly, diarrhea, weight loss, and hematologic abnormalities, including lymphopenia, neutropenia and thrombocytopenia.

Five deaths have occurred in 13 animals (38%) that have been infected with SIV/SMM for at least 14 months. These deaths occurred following prolonged clinical disease characterized by chronic diarrhea and weight loss, peripheral lymphadenopathy and hemogram abnormalities (leukopenia, lymphopenia, neutropenia and thrombocytopenia). Pathologic evaluation revealed severe weight loss (up to 27%), generalized lymphadenopathy and splenomegaly. Histologic findings in lymphoid tissues ranged from prominent follicular hyperplasia to severe lymphoid depletion. Lymphoid tissues often showed a diffuse infiltrate of multinucleated giant cells. One animal also had intestinal cryptosporidiosis and brain lesions comparable to those reported in AIDS encephalopathy of humans. The latter animal never had detectable levels of antibodies to gag region proteins at any time during infection, but did have high levels of env-specific antibodies throughout infection. Animals that showed progressive deterioration of their clinical conditions also showed prominent immunologic changes that were characterized primarily by progressive decreases in total T cells and T-helper cells, with a marked decrease in the T-helper/T-suppressor cell ratio.

To determine whether the pathogenicity or virulence of SIV/SMM might be increased following passage through a macaque monkey, whole blood was collected from animal PBj (pig-tailed macaque that died at 14 months post-infection from an AIDS-like disease) just prior to death, and 10 ml of blood was transfused intravenously into each of three young pig-tailed macaques. All 3 blood transfusion recipients developed acute, fulminating clinical disease within 5 days; the clinical disease was characterized primarily by lethargy and voluminous watery to mucoid diarrhea that contained some blood. All 3 animals were treated intensively with broad spectrum antibiotics (Amikacin, Chloromycetin, Tricarccillin) and fluids. Two of the animals failed to respond to treatment; one died at 8 days post-transfusion (animal PTi) and one died at 9 days post-transfusion (animal POj). Hemogram evaluation of these two animals one day prior to death revealed slight anemia and a marked left shift in the white blood cell differential (19% and 24% bands). One animal (POj) had a normal white blood cell count (7,700), whereas the other animal (PTi) was leukopenic (3,200) and lymphopenic (1,344). Multiple specimens (blood, liver, spleen) taken from both animals for bacterial culture were culture negative. A blood specimen taken from one animal (PTi) prior to any treatment with antibiotics was also culture negative. At necropsy, both of these animals were dehydrated and showed severe generalized lymphadenopathy and splenomegaly and mild to moderate pulmonary edema. Peyer's patches in the small intestine were hyperplastic and very prominent; lymphoid foci in the mucosa of the colon were also very prominent. Histologic examination of tissue sections from these two cases revealed prominent hyperplasia of virtually all lymphoid-associated tissues throughout the body. Prominent paracortical expansion of lymph nodes was the consistent feature with germinal centers usually indistinct or consisting only of poorly defined pale hyalinized areas.

In one case (PTi), examination of periaortic, mesenteric and colonic lymph node sections revealed few to relatively numerous Langhan's-type giant cells. Acid-fast and PAS stains were negative for mycobacterial and fungal organisms. Prominent splenic follicles were evident in both cases with prominently hyalinized germinal centers. The Peyer's patches were very hyperplastic in both animals with small numbers of syncytial cells seen in tissue from POj. Lymphoid tissue in the colon and small intestine of both animals was very prominent with many multinucleated and Langhan's type giant cells seen in sections of colon from PTi. In addition, syncytial cells were observed in gastric mucosal lymphoid tissue from POj. Other findings included focal to relatively diffuse lymphoreticular hyperplasia of the lamina propria of the small intestine and colon with scattered crypts throughout portions of the small intestine and colon containing small amounts of cellular and neutrophilic debris. Hyperplasia of tonsillar tissue and thymic depletion were also evident. The cause of death was attributed to severe dehydration and electrolyte imbalance which resulted from intestinal lesions.

The third blood transfusion recipient (animal PWi) developed a similar acute clinical disease syndrome, but appeared to respond slowly to intense broad spectrum antibiotic therapy. This animal also showed epistaxis of varying degrees from day 12 to day 18 post-transfusion. Animal PWi developed severe oral candidiasis and showed a 14.1% weight loss during the 21 day period following receipt of the blood transfusion. A hemogram evaluation 3 weeks after the blood transfusion revealed anemia (Hcrt. of 25.3), a WBC count of 13,200 with 3% band neutrophils and 15% monocytes, and mild thrombocytopenia (platelet count of 133,000). At sixty-six days post-transfusion, this animal became lethargic and developed a watery diarrhea. Four days later, she appeared to be disoriented and showed intermittent stumbling and circling to the right. She was subsequently sacrificed 70 days post-transfusion due to her deteriorating clinical condition and the development of signs of CNS disease. A hemogram evaluation just prior to death revealed an anemia (Hcrt. of 32.9) and leukopenia (WBC of 3,500) with severe lymphopenia (absolute lymphocyte count of 735) and monocytosis (12%). The platelet count was 203,000.

At autopsy, the animal showed severe generalized lymphadenopathy, splenomegaly and oroesophageal candidiasis. Histologic examination of tissue sections from this animal revealed mild to moderate lymphoid depletion with prominent numbers of syncytial and Langhan's type giant cells, similar to those seen in PBj, throughout all the lymph nodes with infiltration of similar cells throughout the liver, within the lamina propria and submucosa of the colon and small intestine, predominantly in gut-associated lymphoid tissue, and within adipose tissue surrounding many organs and tissues. Fewer giant cells were within the spleen, tonsil and stomach. Examination of multiple brain sections revealed moderate numbers of giant cells throughout meningeal tissues. Lesions within brain parenchyma were minimal.

Virus isolated from animals that died acutely was inoculated intravenously into 6 pig-tailed macaques, 3 rhesus monkeys and 3 young, seronegative mangabeys. Diarrheal material from the animals dying acute deaths was also administered by nasogastric intubation to 3 young pig-tailed macaques. All of the pig-tailed macaques and mangabeys, and one of three rhesus monkeys that received virus by intravenous inoculation, developed acute clinical disease and died within 2 weeks or less. One of three pig-tailed macaques that received diarrheal material by nasogastric intubation developed acute clinical disease and died 12 days post-exposure. All of these animals had clinical disease and gross and microscopic lesions that were essentially identical to those described above for the blood transfusion recipients. Retrovirus was isolated from blood and multiple tissues of all animals that died acutely.

III. SUMMARY

A high incidence of infection with a T-lymphotropic retrovirus has been documented in the Yerkes mangabey breeding colony; 88% of adults and 50% of animals less than four years old are seropositive. Although infected mangabeys are clinically normal, occasional spontaneous diseases are seen that could be associated with an immunosuppressive virus infection. Rhesus and pig-tailed macaques are readily susceptible to experimental infection with SIV/SMM and develop variable degrees of hemogram abnormalities, lymphadenopathy, splenomegaly, diarrhea and weight loss. Thirty-eight of the macaques infected for 14 months or longer have died from an AIDS-like disease. Recent transmission studies using whole blood from a chronically infected pig-tailed macaque resulted in acute, rapidly progressive fatal disease in the transfusion recipients. Virus isolated from animals that died acutely, produced identical disease when inoculated intravenously into 6 additional pig-tailed macaques. This more virulent strain of virus (SIV/SMM/PBj14) was subsequently shown to produce acute, fatal disease in young, seronegative mangabeys (3 of 3) and young rhesus macaques (1 of 3), when inoculated intravenously. Additional studies with young pig-tailed macaques have indicated that this infection can be transmitted by the fecal-oral route. The lethal variant appears to replicate more efficiently in vitro than the original SIV/SMM isolate and also appears to have escaped immune surveillance by alteration of neutralizing epitopes. The latter conclusion is based on the fact that SIV/SMM, but not SIV/SMM/PBMj14 is neutralized by serum from PBJ obtained at the time of death.

A biological deposit of the virus SIV/SMM/PBj14 (PBj14) was made with the Patent Culture Depository of the American Type Culture Collection (ATCC), 12301 parklawn Drive, Rockville, Md. 20852 U.S.A., on Jul. 2, 1991. viability was established by the ATCC as of Sep. 25, 1991. The ATCC accession number of the deposit of SIV/SMM/PBj14 is VR 2331.

It should be seen, therefore, that the present invention provides an effective model for evaluating the antiretroviral effects of newly developed drugs and vaccines. Furthermore, the lethal HIV-like virus isolated by the present inventors is a great asset for studies designed to evaluate newly developed antiretroviral drugs and vaccines.

What is claimed is:

1. SIV/SMM/PBj14, deposited with the American Type Culture Collection under ATCC Accession No. VR 2331, a T-lymphotropic retrovirus taken from a simian primate and capable of inducing acute disease and rapid death upon placement into a second simian primate.

* * * * *